(12) United States Patent
Matsuda

(10) Patent No.: US 11,647,893 B2
(45) Date of Patent: May 16, 2023

(54) ENDOSCOPE

(71) Applicants: Fujikura Ltd., Tokyo (JP); FiberTech Co., Ltd., Chiba (JP)

(72) Inventor: Yusuke Matsuda, Sakura (JP)

(73) Assignees: Fujikura Ltd., Tokyo (JP); FiberTech Co., Ltd., Chiba (JP)

( * ) Notice: Subject to any disclaimer, the term of this patent is extended or adjusted under 35 U.S.C. 154(b) by 41 days.

(21) Appl. No.: 17/211,293

(22) Filed: Mar. 24, 2021

(65) Prior Publication Data

US 2021/0298573 A1    Sep. 30, 2021

(30) Foreign Application Priority Data

Mar. 26, 2020    (JP) .............................. JP2020-056094

(51) Int. Cl.
*A61B 1/00*    (2006.01)

(52) U.S. Cl.
CPC ...... *A61B 1/00096* (2013.01); *A61B 1/00142* (2013.01)

(58) Field of Classification Search
CPC ............ A61B 1/00096; A61B 1/00142; A61B 1/00137; A61B 1/051; G02B 23/242
See application file for complete search history.

(56) References Cited

U.S. PATENT DOCUMENTS

| 2011/0073385 | A1* | 3/2011 | Ko | G06F 3/03542 345/179 |
| 2013/0301148 | A1* | 11/2013 | Breidenthal | A61B 1/00096 359/819 |
| 2013/0342924 | A1* | 12/2013 | Matsuno | G02B 13/0085 264/2.6 |
| 2015/0062316 | A1* | 3/2015 | Haraguchi | A61B 1/00165 359/513 |
| 2015/0316742 | A1* | 11/2015 | Jono | G02B 23/2476 359/830 |
| 2020/0178765 | A1* | 6/2020 | Sato | A61B 1/00186 |

FOREIGN PATENT DOCUMENTS

JP    H05-273474 A    10/1993

\* cited by examiner

*Primary Examiner* — Timothy J Neal
*Assistant Examiner* — Sung Ham
(74) *Attorney, Agent, or Firm* — Osha Bergman Watanabe & Burton LLP

(57) ABSTRACT

An endoscope includes an insertion observation portion including a distal end portion to be inserted into a target object; an objective lens portion disposed on the distal end portion of the insertion observation portion and includes a lens; a holding member that holds the objective lens portion; a sheath that covers the objective lens portion and the holding member; and a sealing material that is disposed on an outer circumference of the objective lens portion and that shields light. A part of the sealing material is disposed on an inner side of a recessed portion of the lens and forms a diaphragm portion that widens a depth of field of the endoscope.

5 Claims, 4 Drawing Sheets

ENDOSCOPE

CROSS-REFERENCE TO RELATED APPLICATIONS

Priority is claimed from Japanese Patent Application No. 2020-056094, filed on Mar. 26, 2020, the content of which is incorporated herein by reference.

TECHNICAL FIELD

The present invention relates to an endoscope.

BACKGROUND

Japanese Patent Application No. H5-273474 discloses an endoscope which includes an objective lens portion provided at a distal end portion of an insertion observation portion, and a diaphragm portion (aperture diaphragm) that regulates the amount of light entering the objective lens portion from a distal end surface of the insertion observation portion. The diaphragm portion is positioned by abutting the other members.

In a case where the diaphragm portion is positioned by abutting the other members as in the related art, when trying to make the insertion observation portion smaller in diameter, the member of the diaphragm portion becomes minute so that it is difficult to accurately position the diaphragm portion. Therefore, the positioning of the diaphragm portion has been an issue in realizing a reduction in diameter of the insertion observation portion.

SUMMARY

One or more embodiments of the present invention reduce a diameter of an insertion observation portion of an endoscope.

An endoscope according to one or more embodiments of the present invention includes an objective lens portion that is provided on a distal end portion of an insertion observation portion and includes at least one lens; a holding member that holds the objective lens portion; a sheath that covers the objective lens portion and the holding member; and a sealing material that is arranged on an outer circumference of the objective lens portion and has a light shielding property, in which a part of the sealing material is positioned on an inner side of a recessed portion of the lens to form a diaphragm portion.

According to one or more embodiments of the present invention, by arranging the sealing material in a state of having fluidity, on the outer circumference of the objective lens portion, and curing the sealing material in a state where part of the sealing material has entered the recessed portion, the diaphragm portion corresponding to the shape of the recessed portion can be easily formed. Accordingly, even when the size of the diaphragm portion becomes minute, it is possible to improve the positioning accuracy of the diaphragm portion as compared with a case where the diaphragm portion is positioned by abutting against the other members as in the related art. Therefore, it is possible to realize a reduction in diameter of the insertion observation portion of the endoscope.

Here, the sealing material may be a black resin.

Further, the holding member may have a cylindrical shape.

Further, the recessed portion may be recessed from a front surface of the lens to a rear side of the lens.

Further, the recessed portion may be recessed inwardly from a side surface of the lens in a radial direction.

According to one or more embodiments of the present invention, it is possible to realize a reduction in diameter of the insertion observation portion of the endoscope.

DETAILED DESCRIPTION OF THE DRAWINGS

DETAILED DESCRIPTION

First Embodiment

Hereinafter, an endoscope of a first embodiment will be described with reference to the drawings.

Figure 1:
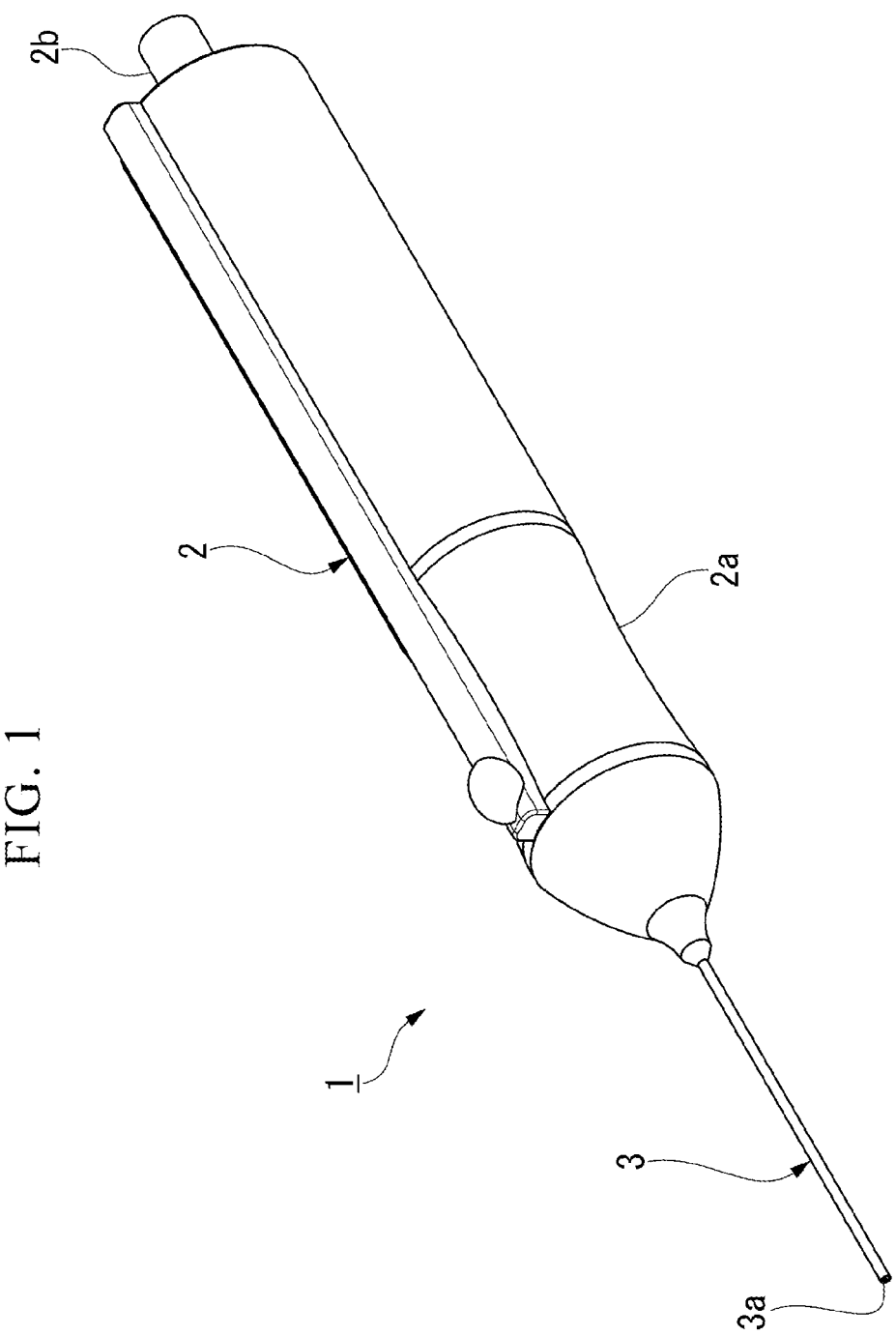
FIG. 1 is a perspective view of an endoscope according to a first embodiment.

As illustrated in FIG. 1, an endoscope 1 includes an operation portion 2, and an insertion observation portion 3 that extends forward from the operation portion 2. The operation portion 2 has a grip portion 2a to be gripped by a user. A cable 2b extends on a rear side of the operation portion 2. Image data or the like obtained from the insertion observation portion 3 is transferred to an image processing unit (not illustrated) via the cable 2b. The image processing unit displays an image on a monitor or stores the image in a storage medium.

Figure 2:
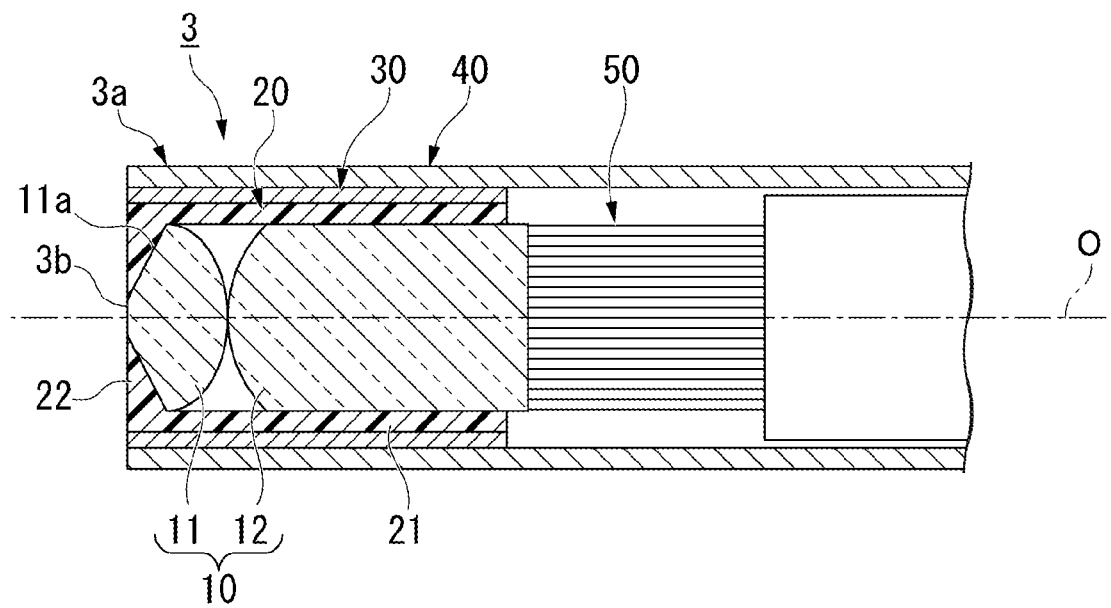
FIG. 2 is a sectional view of an insertion observation portion according to the first embodiment.

The insertion observation portion 3 is formed in an elongated needle shape. As illustrated in FIG. 2, the insertion observation portion 3 includes an objective lens portion 10, a sealing material 20, a holding member 30, a sheath 40, and a transfer unit 50. The objective lens portion 10, the sealing material 20, and the holding member 30 are provided on an inner side of the sheath 40 at a distal end portion 3a of the insertion observation portion 3. The distal end portion 3a is a portion on a distal end side which is to be inserted into a target object (inside the body of a patient or the like) when the endoscope 1 is used.

Direction Definition

In the first embodiment, a direction in which a central axis O of the insertion observation portion 3 extends is referred to as a longitudinal direction. In the longitudinal direction, a side closer to the distal end portion 3a is referred to as a front side, and a side opposite thereto is referred to as a rear side. When viewed from the longitudinal direction, a direction that orbits around the central axis O is referred to as a circumferential direction, and a direction intersecting the central axis O is referred to as a radial direction.

FIG. 2 or the like is a sectional view of the insertion observation portion 3 along the longitudinal direction.

The objective lens portion 10 includes a first lens 11 and a second lens 12. The number of lenses constituting the objective lens portion 10 can be appropriately changed.

The first lens 11 is positioned in front of the second lens 12. An end surface (front surface) on the front side of the first lens 11 is flat surface at least in a central portion in the radial direction. In the first embodiment, a recessed portion 11a is formed to be recessed from the front surface of the first lens 11 to the rear side of the first lens 11. The recessed portion 11a is formed such that the depth thereof from the front surface of the first lens 11 in the longitudinal direction becomes deeper toward the outside in the radial direction. The recessed portion 11a is formed in an annular shape when viewed from the longitudinal direction. The front surface of the first lens 11 constitutes a distal end surface 3b of the distal end portion 3a of the insertion observation portion 3.

An end surface (rear surface) on the rear side of the first lens 11 is a curved surface which is convex to the rear side. A front surface of the second lens 12 is a curved surface which is convex to the front side. A gap (air gap) is provided between the rear surface of the first lens 11 and the front surface of the second lens 12. The length of the gap (air gap) in the longitudinal direction is increased toward the outside in the radial direction. The rear surface of the first lens 11 and the front surface of the second lens 12 are in contact with each other at the central portion in the radial direction.

The transfer unit 50 is connected to a rear end of the objective lens portion 10 (that is, a rear end of the second lens 12). The transfer unit 50 transfers light, which has entered the objective lens portion 10 from the distal end surface 3b of the distal end portion 3a, to the cable 2b connected to the rear end of the endoscope 1. The transfer unit 50 of the first embodiment is a multi-core fiber (image fiber) in which a plurality of optical fibers are integrated. The configuration of the transfer unit 50 may be appropriately changed.

The holding member 30 holds the objective lens portion 10. The holding member 30 of the first embodiment has a cylindrical shape coaxial with the central axis O. Examples of the material for the holding member 30 include plastics, ceramics, and metals.

The sheath 40 is formed in a cylindrical shape. The sheath 40 covers the objective lens portion 10 and the holding member 30. As the material for the sheath 40, metals such as stainless steel (for example, SUS304), plastics, ceramics, or the like can be used.

The sealing material 20 has a light shielding property, and fills the gap between the holding member 30 and the objective lens portion 10. As the sealing material 20, any material that is curable after filling the gap between the holding member 30 and the objective lens portion 10 in a state of having fluidity may be used. As the sealing material 20, for example, a black resin may be used. Specifically, epoxy resin, acrylic resin, urethane resin, and the like colored in black may be used. The sealing material 20 has an outer circumferential portion 21 which is positioned in the gap in the radial direction between the objective lens portion 10 and the holding member 30, and a diaphragm portion 22 which is positioned in the recessed portion 11a of the first lens 11.

Since the diaphragm portion 22 is formed by a part of the sealing material 20 entering the recessed portion 11a, the diaphragm portion 22 has the same shape as the recessed portion 11a. That is, the diaphragm portion 22 is formed in an annular shape when viewed from the longitudinal direction, and the thickness thereof in the longitudinal direction is increased toward the outside in the radial direction. Among light rays trying to enter the objective lens portion 10 from the distal end surface 3b of the distal end portion 3a, light on the outer circumferential portion is blocked by the diaphragm portion 22. In other words, only the light passing through the inner side of the diaphragm portion 22 in the radial direction enters the objective lens portion 10 from the distal end surface 3b. By providing such a diaphragm portion 22, it is possible to widen the depth of field of the endoscope 1. Further, since the light entering the objective lens portion 10 from the outer circumferential portion of the distal end surface 3b includes a large amount of unnecessary light that does not contribute to the formation of an image, it is possible to improve the contrast of the image by blocking such unnecessary light.

As described above, the endoscope 1 of the first embodiment includes the objective lens portion 10 that is provided on the distal end portion 3a of the insertion observation portion 3 and includes at least one lens (first lens 11); the holding member 30 that holds the objective lens portion 10; the sheath 40 that covers the objective lens portion 10 and the holding member 30; and the sealing material 20 that is arranged on an outer circumference of the objective lens portion 10 and has a light shielding property. A part of the sealing material 20 is positioned on an inner side of the recessed portion 11a of the first lens 11 to form the diaphragm portion 22.

According to the configuration, by arranging the sealing material 20 in a state of having fluidity, on the outer circumference of the objective lens portion 10, and curing the sealing material 20 in a state where a part of the sealing material 20 has entered the recessed portion 11a, the diaphragm portion 22 corresponding to the shape of the recessed portion 11a can be easily formed. Accordingly, even when the size of the diaphragm portion 22 becomes minute, it is possible to improve the positioning accuracy of the diaphragm portion 22 as compared with a case where the diaphragm portion is positioned by abutting against the other members as in the related art. Therefore, it is possible to realize a reduction in diameter of the insertion observation portion 3. Further, the cost can be reduced as compared with a case where the diaphragm portion 22 is configured as a separate member.

The sealing material 20 may be a black resin. The black resin is suitable as the material for the sealing material 20, because the black resin has a light shielding property. The resin forming the sealing material 20 may have fluidity when the resin is filled in the gap on the outer circumference of the objective lens portion 10. In this case, it is easy to cure the resin after the resin fills the gap on the outer circumference of the objective lens portion 10. Therefore, the black resin having fluidity when the resin is filled in the gap is suitable as the material for the sealing material 20.

Further, in a case where the holding member 30 has a cylindrical shape, it is easy to arrange the objective lens portion 10 and the diaphragm portion 22 coaxially with the central axis O of the insertion observation portion 3. Therefore, the deviation of the optical axis of the light passing through the diaphragm portion 22 and entering the objective lens portion 10 is reduced, and it is possible to form an image with higher accuracy.

Figure 3:
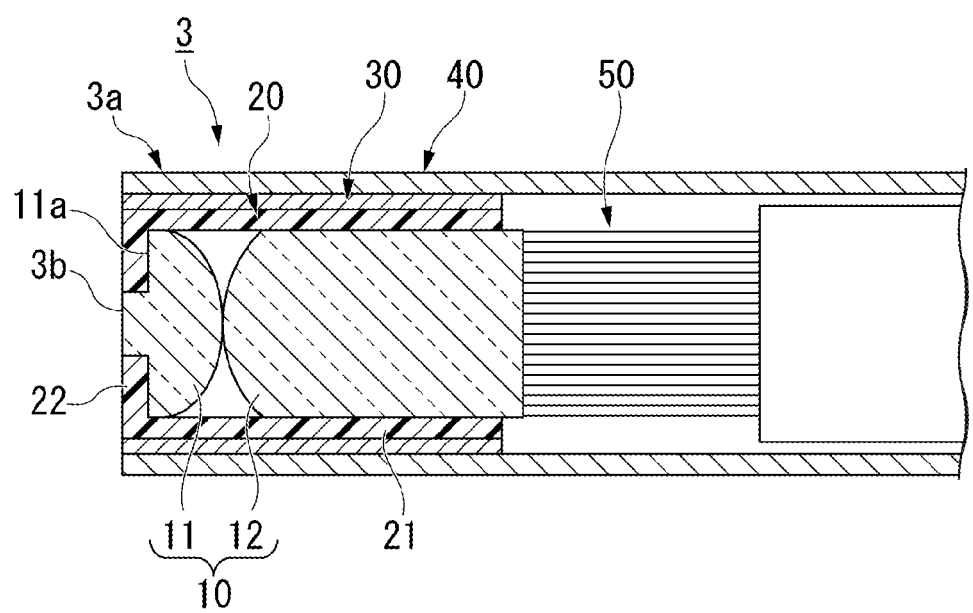
FIG. 3 is a sectional view of an insertion observation portion according to a modification example of the first embodiment.
Figure 4:
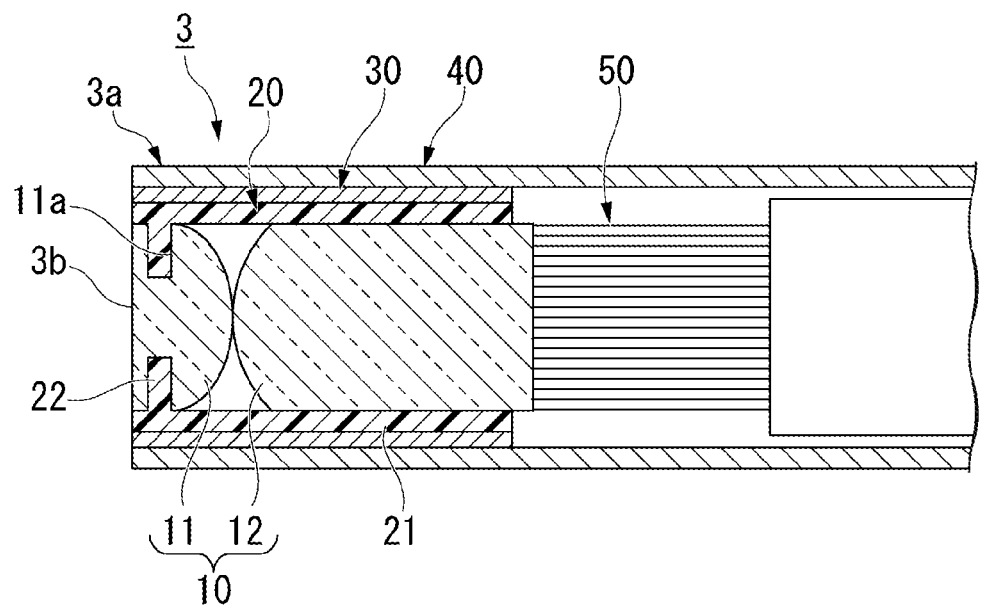
FIG. 4 is a sectional view of an insertion observation portion according to another modification example of the first embodiment.

The recessed portion 11a of the first embodiment is recessed from the front surface of the first lens 11 to the rear side of the first lens 11, and the depth thereof in the longitudinal direction is increased toward the outside in the radial direction. The shape or position of the recessed portion 11a (that is, the diaphragm portion 22) can be appropriately changed. For example, as illustrated in FIG. 3, the depth of the recessed portion 11a in the longitudinal direction may be uniform along the radial direction. Further, as illustrated in FIG. 4, the recessed portion 11a may be an annular groove which is recessed inwardly from the side surface (outer circumferential surface) of the first lens 11 in the radial direction. Even in these cases, similar effects are obtained.

Second Embodiment

Next, a second embodiment according to the present invention will be described, but the basic configuration thereof is similar to that of the first embodiment. Therefore, the same reference numerals are given to the same configurations, the description thereof will be omitted, and only the different points will be described.

Figure 5:
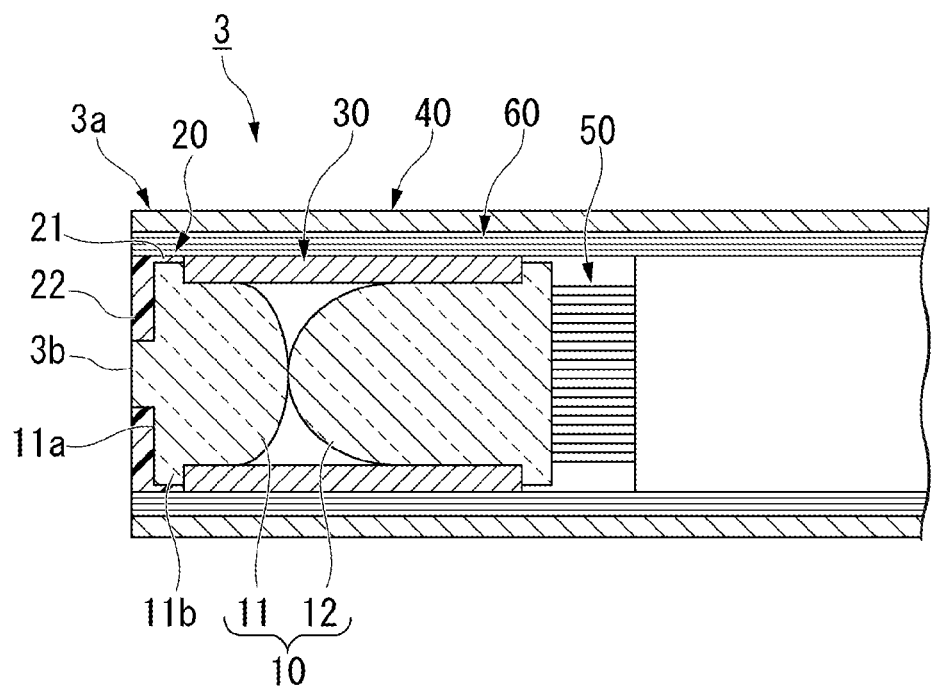
FIG. 5 is a sectional view of an insertion observation portion according to a second embodiment.

As illustrated in FIG. 5, the endoscope 1 of the second embodiment includes a light guide fiber 60. The light guide fiber 60 is configured to launch light, which is launched from a light source connected to the rear side of the endoscope 1, from the distal end surface 3b of the distal end portion 3a. The light guide fiber 60 is positioned on the outer side of the holding member 30 and the sealing material 20 in the radial direction and on the inner side of the sheath 40 in the radial direction.

Further, the first lens 11 of the second embodiment has an annular flange portion 11b that protrudes to the outside in the radial direction. The flange portion 11b is positioned in front of the holding member 30. A gap between the flange portion 11b and the light guide fiber 60 is filled with the sealing material 20.

Also in the second embodiment, a part of the sealing material 20 that fills the gap on the outer circumference of the objective lens portion 10 (gap between the flange portion 11b and the light guide fiber 60) is positioned on the inner side of the recessed portion 11a of the first lens 11 to form the diaphragm portion 22. Accordingly, the effects similar to those of the first embodiment are obtained.

Figure 6:
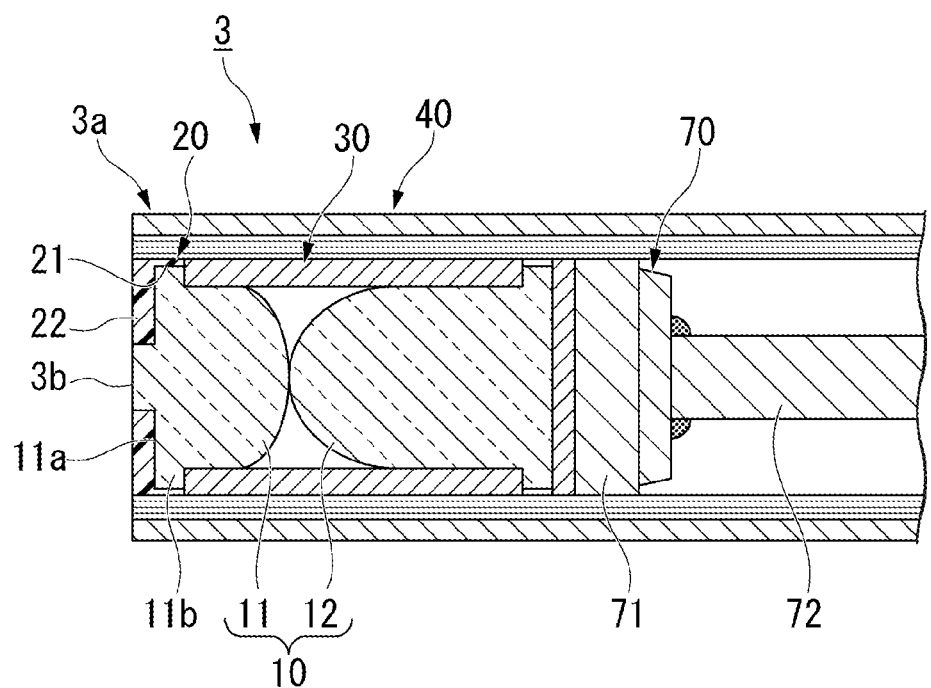
FIG. 6 is a sectional view of an insertion observation portion according to a modification example of the second embodiment.

FIG. 6 illustrates the insertion observation portion 3 of the endoscope 1 according to a modification example of the second embodiment. As illustrated in FIG. 6, an imaging module 70 may be provided behind the objective lens portion 10. The imaging module 70 has an imaging element 71, and a signal line 72. The imaging element 71 is configured to convert an image, which is obtained by the image formation of light received through the objective lens portion 10, to an electric signal. The signal line 72 is housed in the cable 2b (refer to FIG. 1), and is connected to the image processing unit. The image data converted into the electric signal is transferred, through the signal line 72, to the image processing unit or the like connected to the rear side of the endoscope 1. In this manner, instead of the transfer unit 50 such as an image fiber that transfers light, a transfer unit that transfers an electric signal (signal line 72 connected to the imaging element 71) can be used.

The technical scope of the invention is not limited to the embodiments described above, and various changes can be made without departing from the gist of the invention.

For example, in the embodiments, among the first lens 11 and the second lens 12 constituting the objective lens portion 10, the recessed portion 11a is formed in the first lens 11. However, a recessed portion may be formed in the second lens 12, and the diaphragm portion 22 may be formed by causing the sealing material 20 to enter the recessed portion. Similarly, even in a case where the objective lens portion 10 has three or more lenses, the recessed portion may be formed in any of the lenses.

Furthermore, the sealing material 20 may not be disposed in a gap (air gap) between the rear surface of the first lens 11 and the front surface of the second lens 12. Similarly, even in a case where the objective lens portion 10 has three or more lenses, the sealing material 20 may not be disposed in a gap (air gap) between two adjacent lenses.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

EXPLANATION OF REFERENCES

1: endoscope
3: insertion observation portion
3a: distal end portion
10: objective lens portion
11: first lens (lens)
11a: recessed portion
12: second lens (lens)
20: sealing material
22: diaphragm portion
30: holding member
40: sheath

What is claimed is:
1. An endoscope comprising:
an insertion observation portion comprising a distal end portion to be inserted into a target object;
an objective lens portion that is disposed on the distal end portion of the insertion observation portion and comprises a lens;
a holding member that holds the objective lens portion;
a sheath that covers the objective lens portion and the holding member; and
a sealing material that is disposed on an outer circumference of the objective lens portion and that shields light, wherein
a part of the sealing material is disposed on a recessed portion of the lens and forms a diaphragm portion that widens a depth of field of the endoscope, and
the recessed portion of the lens is recessed from a front surface of the lens to a rear side of the lens.
2. The endoscope according to claim 1, wherein the sealing material is a black resin.
3. The endoscope according to claim 1, wherein the holding member has a cylindrical shape.
4. An endoscope comprising:
an insertion observation portion comprising a distal end portion to be inserted into a target object;
an objective lens portion that is disposed on the distal end portion of the insertion observation portion and comprises a lens;
a holding member that holds the objective lens portion;
a sheath that covers the objective lens portion and the holding member; and
a sealing material that is disposed on an outer circumference of the objective lens portion and that shields light, wherein
a part of the sealing material is disposed on a recessed portion of the lens and forms a diaphragm portion that widens a depth of field of the endoscope,
the recessed portion of the lens is recessed inwardly from an outer circumferential surface of the lens in a radial direction and forms an annular groove on the outer circumferential surface of the lens.

5. An endoscope comprising:
- an insertion observation portion comprising a distal end portion to be inserted into a target object;
- an objective lens portion that is disposed on the distal end portion of the insertion observation portion and comprises a lens;
- a holding member that holds the objective lens portion;
- a sheath that covers the objective lens portion and the holding member; and
- a sealing material that is disposed on an outer circumference of the objective lens portion and that shields light, wherein
- a part of the sealing material is disposed on a recessed portion of the lens and forms a diaphragm portion that widens a depth of field of the endoscope,
- the recessed portion is formed in an annular shape when viewed from a longitudinal direction in which a central axis of the insertion observation portion extends,
- a depth of the recessed portion from a front surface of the lens in the longitudinal direction becomes deeper toward an outside in a radial direction of the insertion observation portion,
- a front surface of the insertion observation portion is flat,
- the front surface of the lens is flat, and
- the front surface of the insertion observation portion is flush with respect to the front surface of the lens.

* * * * *